United States Patent
Uda et al.

(10) Patent No.: US 10,752,601 B2
(45) Date of Patent: Aug. 25, 2020

(54) CRYSTAL FORM AND SALT OF 3-(3,5-DICHLORO-4-HYDROXYBENZOYL)-1,1-DIOXO-2,3-DIHYDRO-1,3-BENZOTHIAZOLE

(71) Applicant: FUJI YAKUHIN CO., LTD., Saitama-shi, Saitama (JP)

(72) Inventors: Junichiro Uda, Saitama (JP); Seiichi Kobashi, Saitama (JP); Misa Hasegawa, Saitama (JP)

(73) Assignee: Fuji Yakuhin Co., Ltd, Saitama (JP)

( * ) Notice: Subject to any disclaimer, the term of this patent is extended or adjusted under 35 U.S.C. 154(b) by 0 days.

(21) Appl. No.: 16/482,149

(22) PCT Filed: Apr. 27, 2018

(86) PCT No.: PCT/JP2018/017128
§ 371 (c)(1),
(2) Date: Jul. 30, 2019

(87) PCT Pub. No.: WO2018/199277
PCT Pub. Date: Nov. 1, 2018

(65) Prior Publication Data
US 2019/0389818 A1     Dec. 26, 2019

(30) Foreign Application Priority Data
Apr. 28, 2017   (JP) ................... 2017-099334

(51) Int. Cl.
*C07D 277/62*   (2006.01)

(52) U.S. Cl.
CPC ........ *C07D 277/62* (2013.01); *C07B 2200/13* (2013.01)

(58) Field of Classification Search
CPC .................................................. C07D 277/62
See application file for complete search history.

(56) References Cited

U.S. PATENT DOCUMENTS 8,367,843 B2    2/2013  Kobashi et al.

FOREIGN PATENT DOCUMENTS

| WO | 2006057460 A1 | 6/2006 |
| WO | 2007138998 A1 | 12/2007 |
| WO | 2007139002 A1 | 12/2007 |
| WO | 2011040449 A1 | 4/2011 |

OTHER PUBLICATIONS

Japan Patent Office; International Search Report; dated Jul. 11, 2018.

*Primary Examiner* — Shawquia Jackson
(74) *Attorney, Agent, or Firm* — Price Heneveld LLP (57) ABSTRACT

A type II crystal of 3-(3,5-dichloro-4-hydroxybenzoyl)-1,1-dioxo-2,3-dihydro-1,3-benzothiazole, having characteristic peaks at least around 15.1, 18.1, 22.8, 23.7, and 24.0 degrees in a diffraction angle ($2\theta$) by X-ray powder diffraction, and method for producing said type II crystal.

11 Claims, 9 Drawing Sheets

CRYSTAL FORM AND SALT OF 3-(3,5-DICHLORO-4-HYDROXYBENZOYL)-1,1-DIOXO-2,3-DIHYDRO-1,3-BENZOTHIAZOLE

BACKGROUND OF THE INVENTION

Field of the Invention

The present invention relates to a crystal form and a salt of 3-(3,5-dichloro-4-hydroxybenzoyl)-1,1-dioxo-2,3-dihydro-1,3-benzothiazole, which have a significant uricosuric action.

Description of the Related Art

Crystal forms and salts in medication are known to affect e.g. pharmacological activity, solubility, bioavailability, and stability depending on differences in their physicochemical nature. Therefore, when crystal forms and salts exist as compounds useful as medicine, it is desirable to select a crystal form or a salt with high availability among these to produce medicine.

Recently, 3-(3,5-dichloro-4-hydroxybenzoyl)-1,1-dioxo-2,3-dihydro-1,3-benzothiazole, which has a higher level of unchanged compound in urine than that of existing uricosuric agents and has a significant uricosuric action, has been found (see WO2011/040449).

WO2011/040449, however, does not describe a specific crystal form and salt of 3-(3,5-dichloro-4-hydroxybenzoyl)-1,1-dioxo-2,3-dihydro-1,3-benzothiazole, and it also does not disclose a problem when industrially producing the compound and a suggestion thereof.

SUMMARY OF THE INVENTION

Problem to be Solved by the Invention

Therefore, a subject of the present invention is to provide a novel crystal form, hydrate, solvate or salt of 3-(3,5-dichloro-4-hydroxybenzoyl)-1,1-dioxo-2,3-dihydro-1,3-benzothiazole that is useful as medicine, has an excellent uricosuric action, and moreover has excellent convenience in industrial production.

Means for Solving the Problem

As a result of diligent research to solve the above subject, the present inventors found a crystal form of 3-(3,5-dichloro-4-hydroxybenzoyl)-1,1-dioxo-2,3-dihydro-1,3-benzothiazole, which has a significant uricosuric action, and also has excellent physical properties (particularly, flowability and operativity), thereby completing the present invention.

Figure 1:
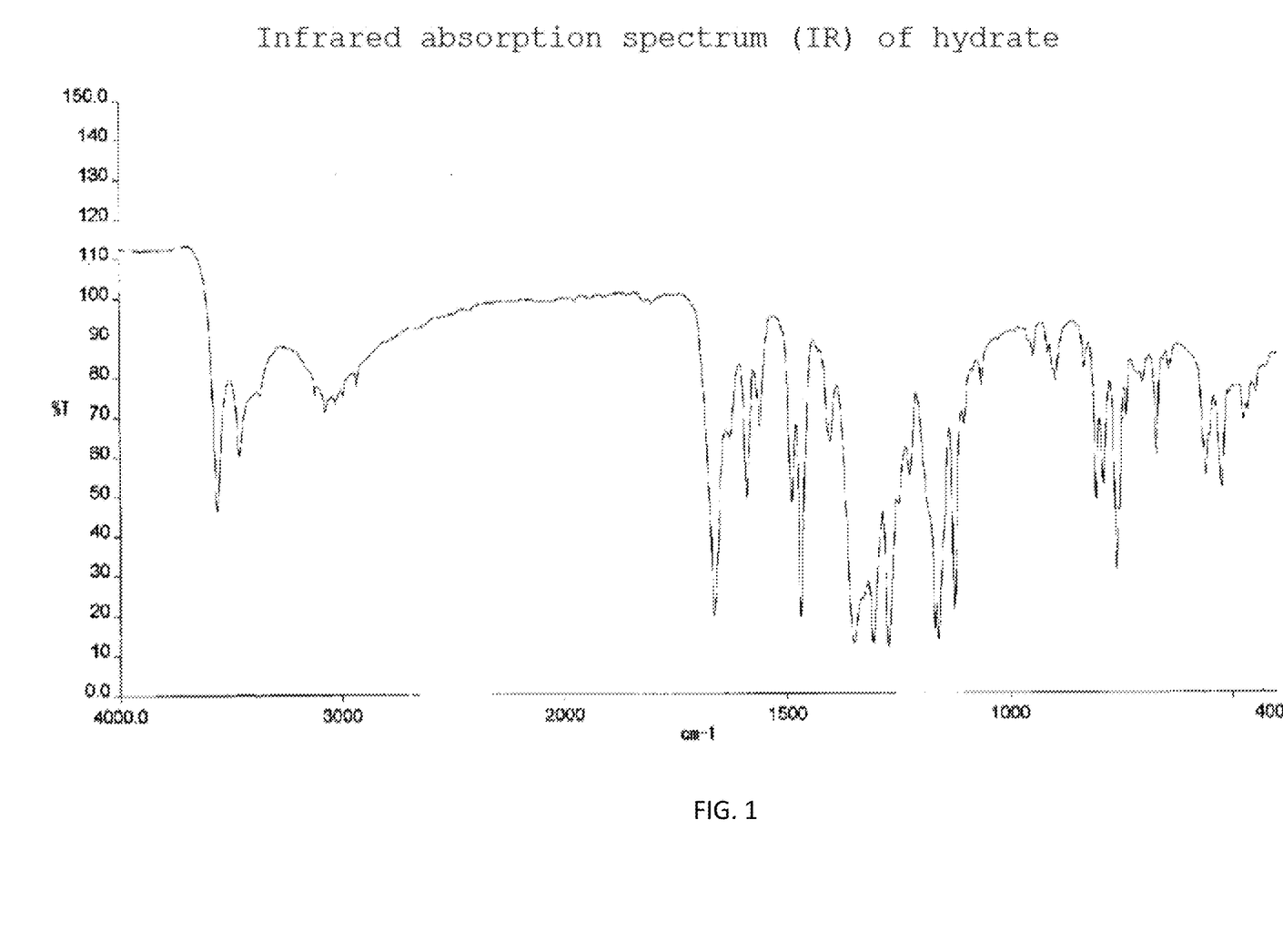
FIG. 1 is X-ray powder diffraction of a type I crystal.
Figure 2:
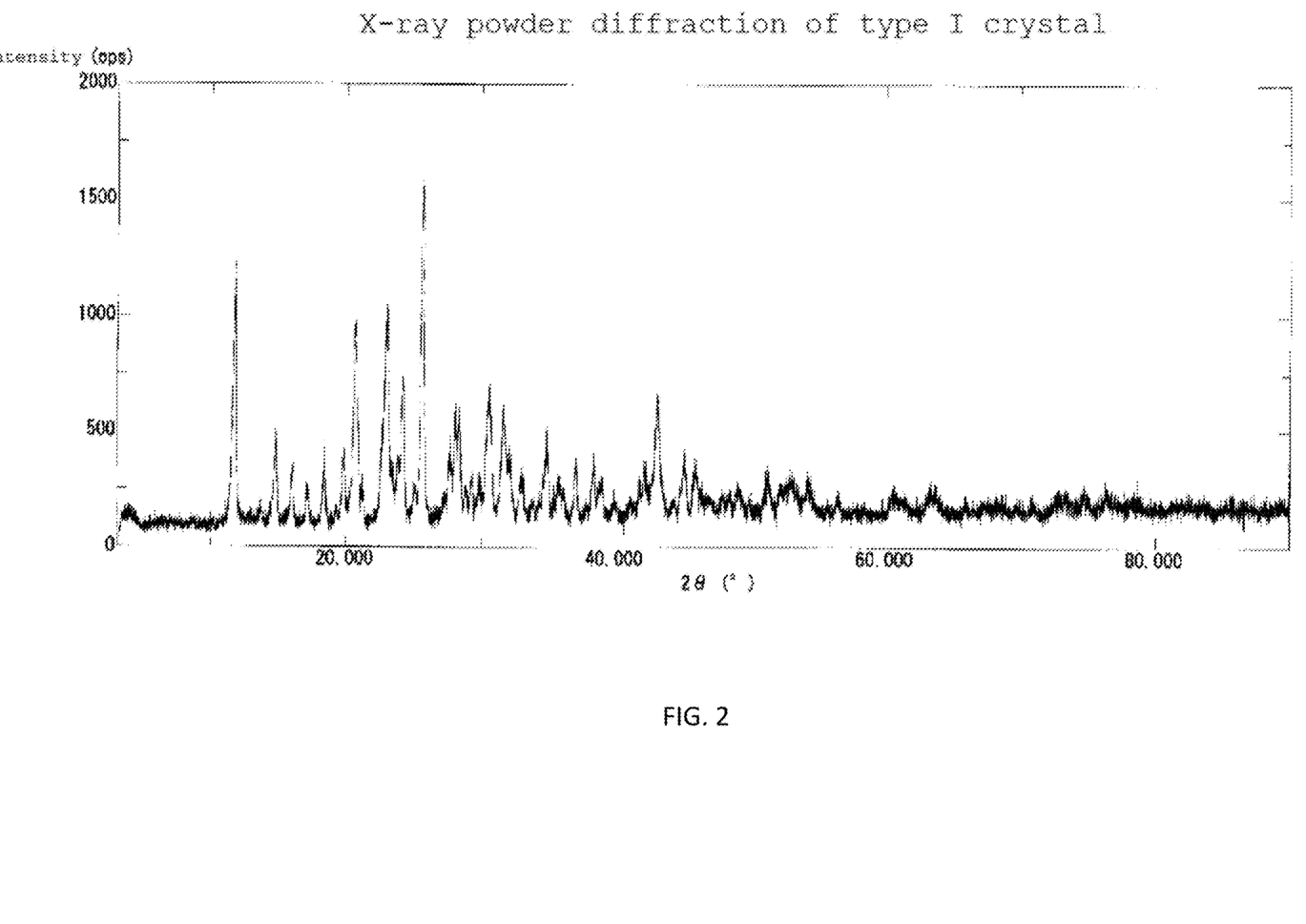
FIG. 2 is X-ray powder diffraction of a type II crystal.
Figure 3:
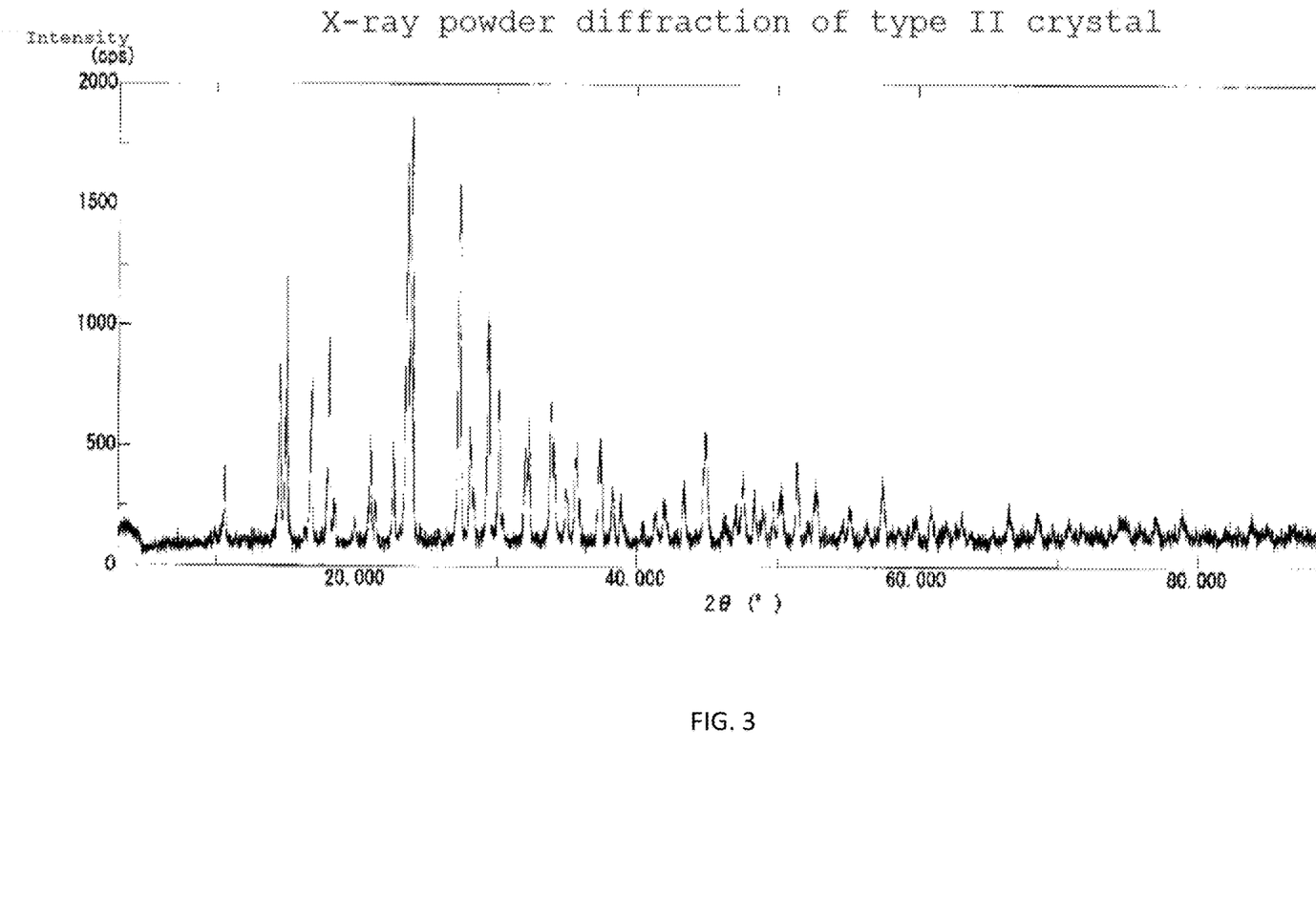
FIG. 3 is X-ray powder diffraction of a hydrate.
Figure 4:
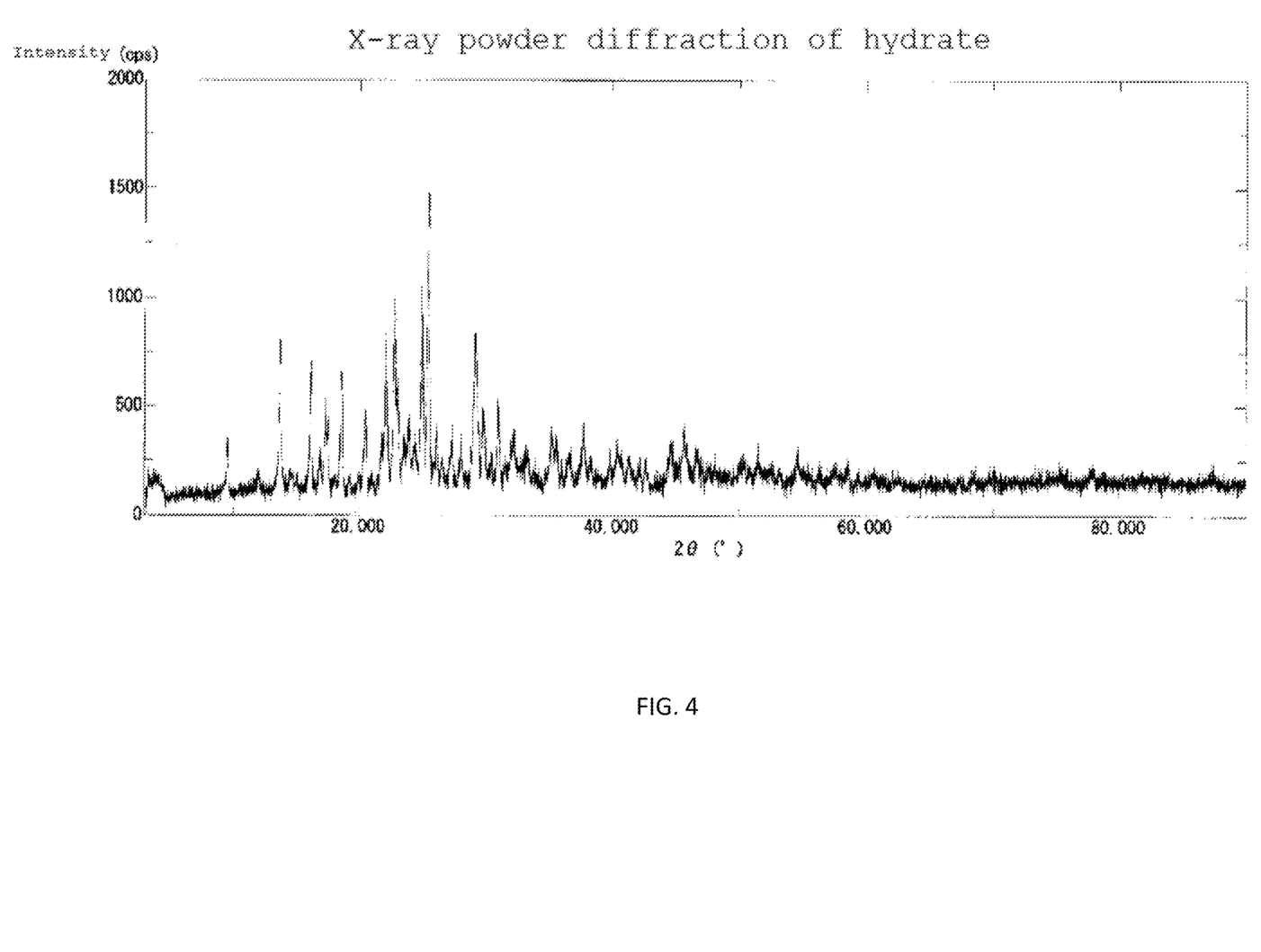
FIG. 4 is thermal analysis (DSC) of a type I crystal.
Figure 5:
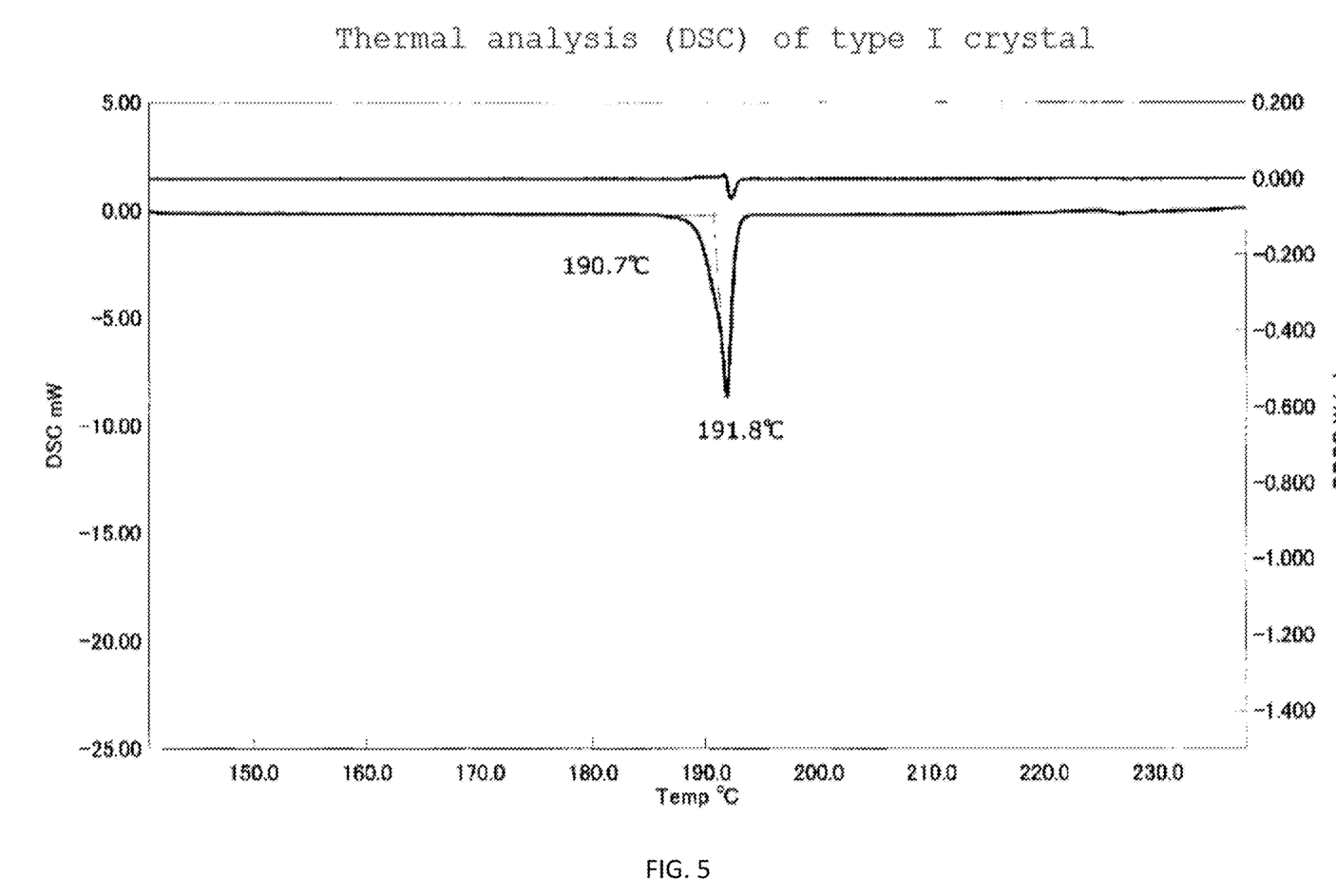
FIG. 5 is thermal analysis (DSC) of a type II crystal.
Figure 6:
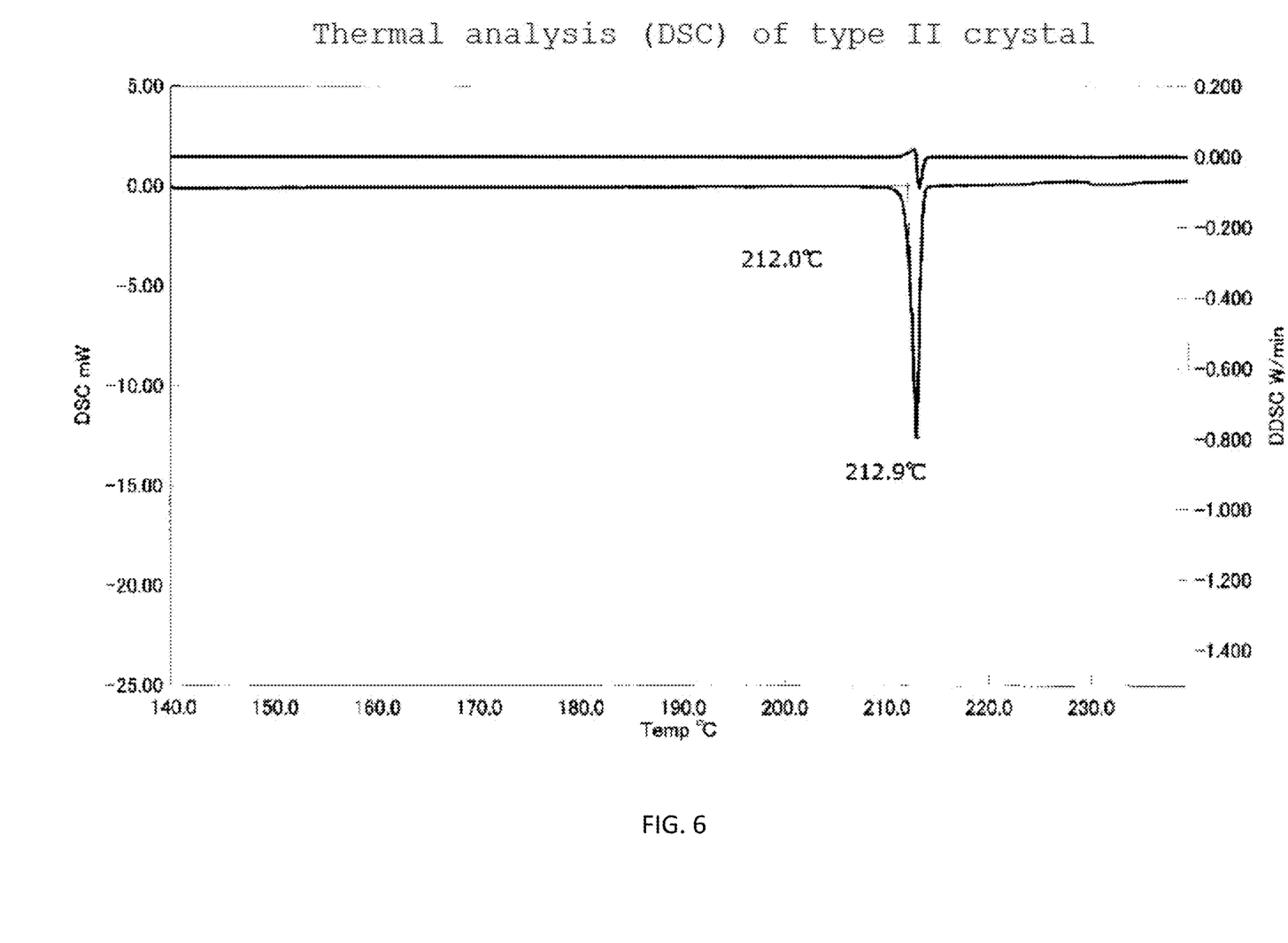
FIG. 6 is thermal analysis (DSC) of a hydrate.
Figure 7:
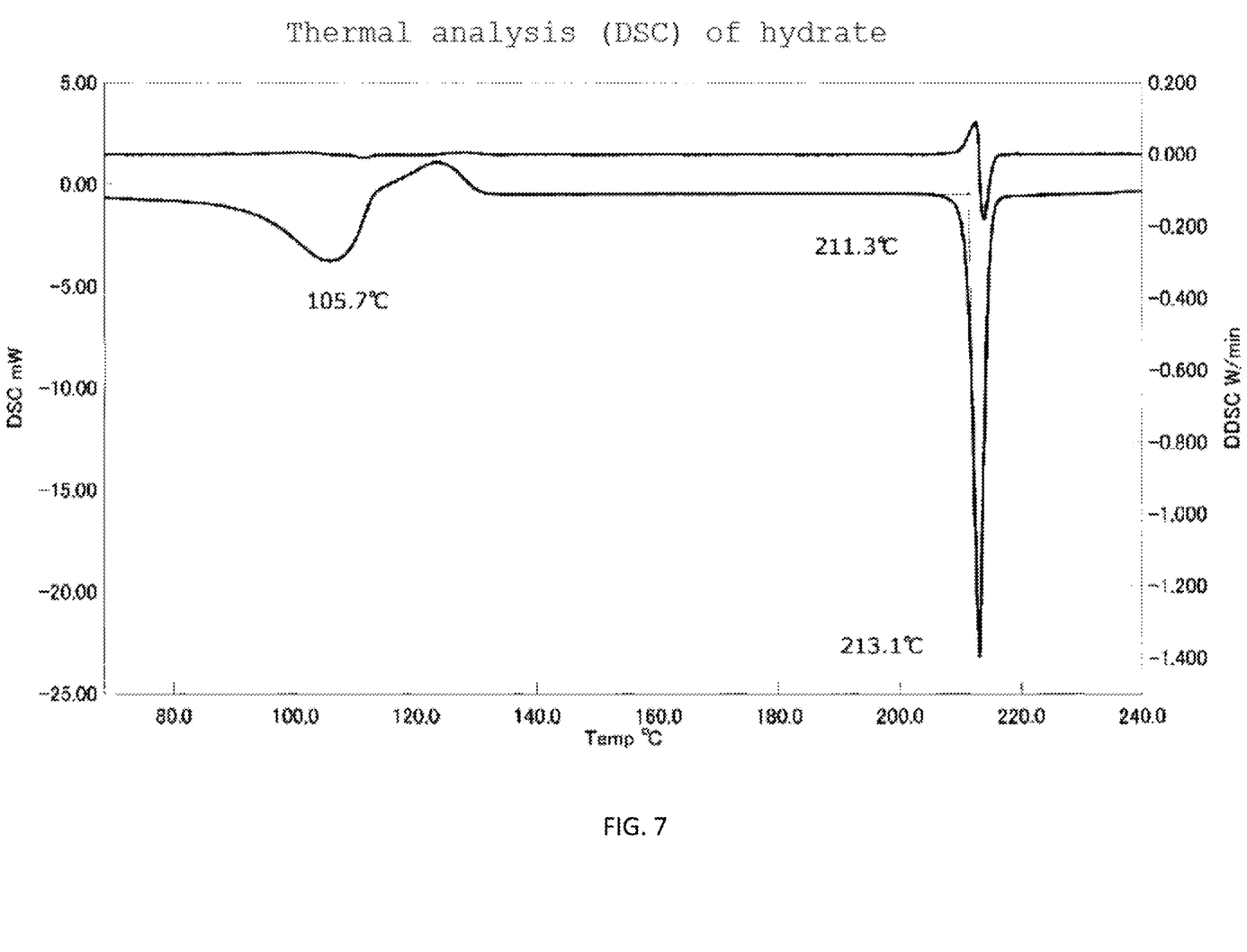
FIG. 7 is an infrared absorption spectrum (IR) of a type I crystal.
Figure 8:
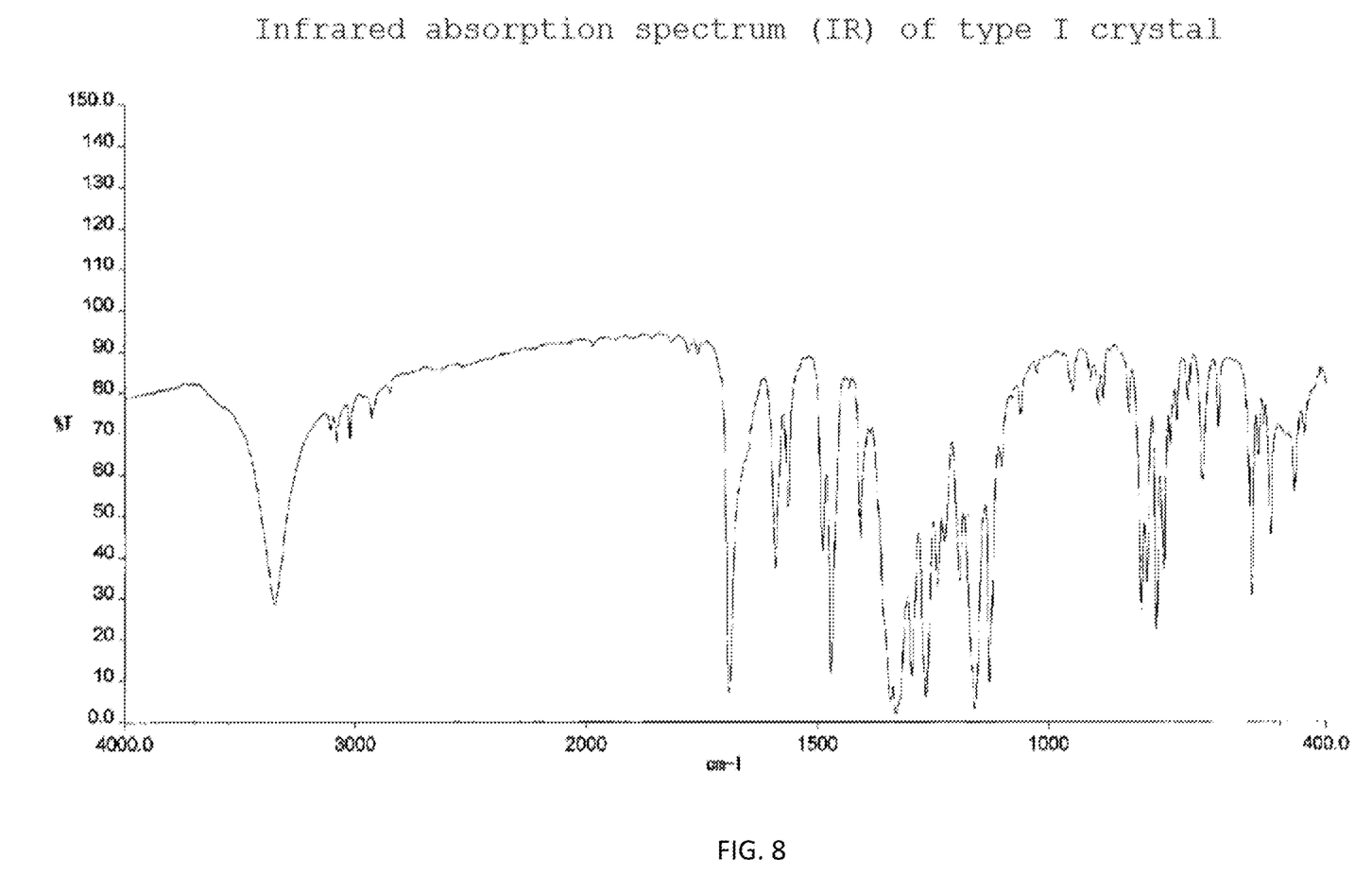
FIG. 8 is an infrared absorption spectrum (IR) of a type II crystal.
Figure 9:
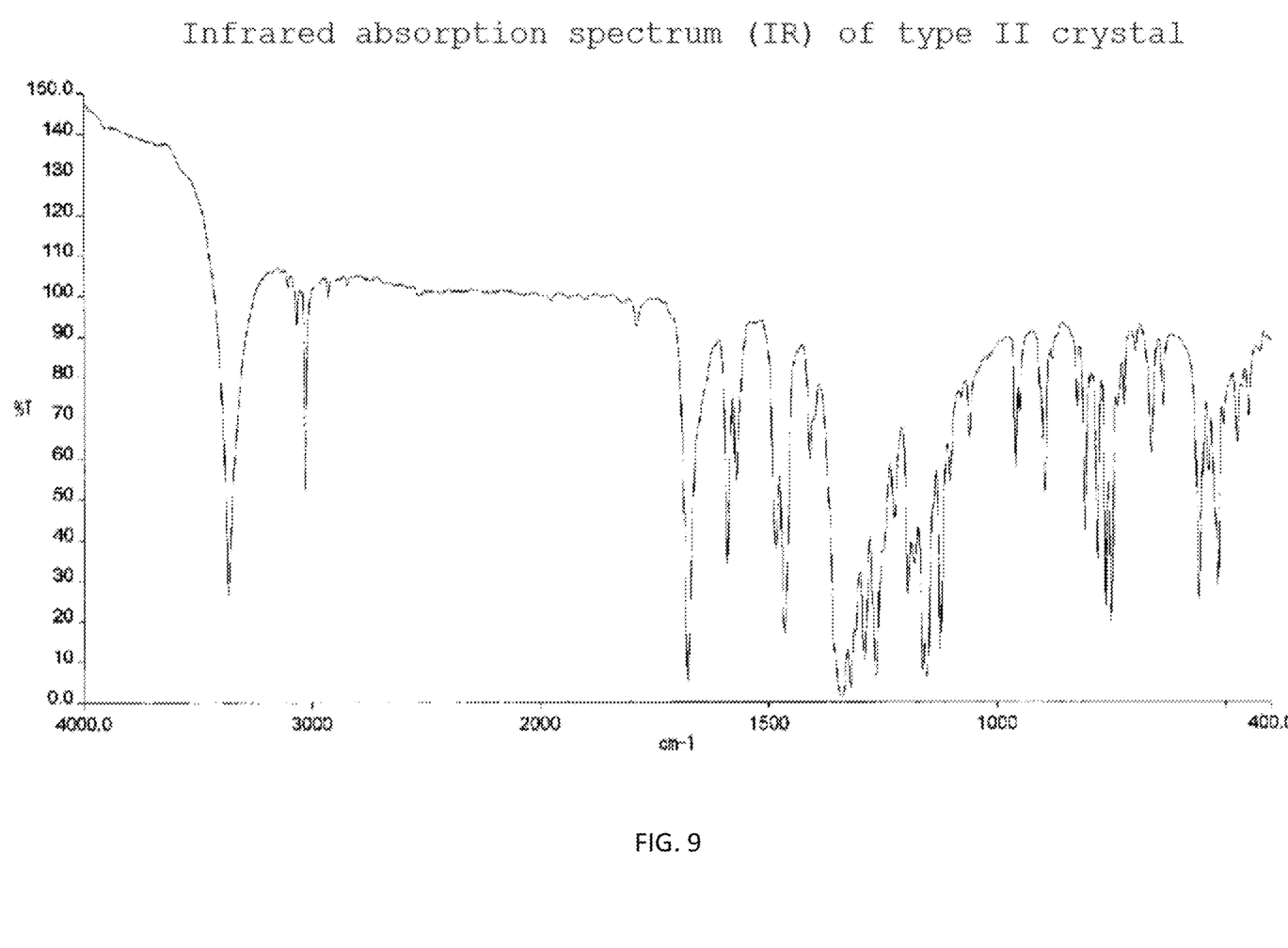
FIG. 9 is an infrared absorption spectrum (IR) of a hydrate.

That is, the present invention relates to:

(1) a type I crystal of 3-(3,5-dichloro-4-hydroxybenzoyl)-1,1-dioxo-2,3-dihydro-1,3-benzothiazole, having characteristic peaks at least around 11.5, 14.6, 18.2, 24.0, and 25.5 degrees in a diffraction angle (2Θ) by X-ray powder diffraction;

(2) a type I crystal of 3-(3,5-dichloro-4-hydroxybenzoyl)-1,1-dioxo-2,3-dihydro-1,3-benzothiazole, characterized by an X-ray powder diffraction diagram shown in FIG. 1;

(3) a type I crystal of 3-(3,5-dichloro-4-hydroxybenzoyl)-1,1-dioxo-2,3-dihydro-1,3-benzothiazole, characterized by having a heat absorption peak around 191° C. in DSC analysis, preferably a type I crystal according to (1) or (2) above;

(4) a type II crystal of 3-(3,5-dichloro-4-hydroxybenzoyl)-1,1-dioxo-2,3-dihydro-1,3-benzothiazole, having characteristic peaks at least around 15.1, 18.1, 22.8, 23.7, and 24.0 degrees in the diffraction angle (2Θ) by X-ray powder diffraction;

(5) a type II crystal of 3-(3,5-dichloro-4-hydroxybenzoyl)-1,1-dioxo-2,3-dihydro-1,3-benzothiazole, characterized by an X-ray powder diffraction diagram shown in FIG. 2;

(6) a type II crystal of 3-(3,5-dichloro-4-hydroxybenzoyl)-1,1-dioxo-2,3-dihydro-1,3-benzothiazole, characterized by having a heat absorption peak around 212° C. in DSC analysis, preferably a type II crystal according to (4) or (5) above;

(7) a hydrate of 3-(3,5-dichloro-4-hydroxybenzoyl)-1,1-dioxo-2,3-dihydro-1,3-benzothiazole, having characteristic peaks at least around 9.5, 13.7, 22.8, 24.9, and 25.3 degrees in the diffraction angle (2Θ) by X-ray powder diffraction;

(8) a hydrate of 3-(3,5-dichloro-4-hydroxybenzoyl)-1,1-dioxo-2,3-dihydro-1,3-benzothiazole, characterized by an X-ray powder diffraction diagram shown in FIG. 3;

(9) a hydrate of 3-(3,5-dichloro-4-hydroxybenzoyl)-1,1-dioxo-2,3-dihydro-1,3-benzothiazole, having heat absorption peaks around 105° C. and 212° C. in DSC analysis, preferably a hydrate according to (7) or (8) above;

(10) a sodium salt of 3-(3,5-dichloro-4-hydroxybenzoyl)-1,1-dioxo-2,3-dihydro-1,3-benzothiazole;

(11) a pharmaceutical composition containing a crystal, a hydrate, or a sodium salt according to any one of (1) to (10) and a pharmaceutically acceptable carrier;

(12) a method for producing a type I crystal according to any one of (1) to (3) above, which is obtained by adding a solution of 3-(3,5-dichloro-4-hydroxybenzoyl)-1,1-dioxo-2,3-dihydro-1,3-benzothiazole in a poor solvent under cooling;

(13) a method for producing a type II crystal according to any one of (4) to (6) above, which can obtain 3-(3,5-dichloro-4-hydroxybenzoyl)-1,1-dioxo-2,3-dihydro-1,3-benzothiazole by crystallization from an organic solvent and drying; and (14) a method for producing a hydrate according to any one of (7) to (9) above, which can be obtained by dissolving 3-(3,5-dichloro-4-hydroxybenzoyl)-1,1-dioxo-2,3-dihydro-1,3-benzothiazole in water or a water/organic solvent mixture by a weak base.

Advantageous Effect of the Invention

The crystal forms, hydrate, solvates, and salt of 3-(3,5-dichloro-4-hydroxybenzoyl)-1,1-dioxo-2,3-dihydro-1,3-benzothiazole in the present invention have an excellent uricosuric action and thus are useful as medication.

The crystals of the present invention are extremely easy to handle in the industrial production and have physical properties with excellent convenience (for example, excellent flowability and operativity), and in particular, a type II crystal also has prepotency in the industrial production and thus is useful as a raw material for medication.

DESCRIPTION OF THE EMBODIMENTS

A method for producing a crystal form of 3-(3,5-dichloro-4-hydroxybenzoyl)-1,1-dioxo-2,3-dihydro-1,3-benzothiazole in the present invention will now be described.

A type I crystal can be produced, for example, by adding dropwise a 3-(3,5-dichloro-4-hydroxybenzoyl)-1,1-dioxo-2,3-dihydro-1,3-benzothiazole dissolved solution in a poor solvent under cooling. As the dissolving solvent, tetrahydrofuran is preferred. Examples of the poor solvent include 2-propanol, ethanol, and n-hexane, and 2-propanol is preferred. It is preferred to use seed crystals at the time of crystallization.

A type II crystal can be obtained, for example, by a method of crystallization from an organic solvent. A method by cooling after dissolution by heating can be used, or a poor solvent can also be used with a dissolving solvent. As the crystallization solvent, for example, dissolving solvents such as ethyl acetate or an ethyl acetate/2-propanol mixed solution, dimethylsulfoxide and heptane, or a mixed solvent of a dissolving solvent and a poor solvent can be used.

A hydrate can be produced, for example, as follows: the above compound is dissolved in water or a water/organic solvent mixture by a weak base such as sodium carbonate and then neutralized using an acid such as hydrochloric acid, and the precipitated crystals are collected by filtration and then dried at a suitable temperature, preferably around 50° C.

A salt can be obtained, for example, as follows: sodium hydroxide, potassium hydroxide, calcium hydroxide, sodium carbonate, potassium carbonate, calcium carbonate or the like is added to a mixture of the above compound and water or water/organic solvent, and an organic solvent is added thereto at the appropriate time, and the obtained solution is stirred under ice cooling to 60° C., preferably around room temperature to 60° C., and the precipitated crystals are collected by filtration and dried at around 50° C. in vacuo. Examples of such salt include a sodium salt, a potassium salt, and a calcium salt.

A solvate can be produced by dissolving the above compound in a polar solvent, followed by crystallization or a combination with a poor solvent. For example, the above compound is dissolved in tetrahydrofuran, 2-methyltetrahydrofuran, dimethoxyethane, 1,4-dioxane, acetone, 2-butanone or the like, and a poor solvent such as n-hexane, cyclohexane, cumene, paraxylene, methylcyclohexane, 2,2,4-trimethylpentane, toluene, n-pentane, 2-propanol, n-heptane, acetonitrile or the like is added thereto to carry out crystallization. A solvate can be produced by drying the obtained crystals at a suitable temperature, preferably around 50° C. More specific examples thereof include a 1,2-dimethoxyethane solvate of 3-(3,5-dichloro-4-hydroxybenzoyl)-1,1-dioxo-2,3-dihydro-1,3-benzothiazole having characteristic peaks around 5.86, 11.98, 20.7, 24.1, and 25.5 in X-ray powder diffraction (2Θ); a 1,4-dioxane solvate of 3-(3,5-dichloro-4-hydroxybenzoyl)-1,1-dioxo-2,3-dihydro-1,3-benzothiazole having characteristic peaks around 8.14, 12.78, 22.54, 24.22, and 25.02 in X-ray powder diffraction (2Θ) and having heat absorption peaks around 153° C., 186° C., and 212° C. in DSC analysis; an acetonitrile solvate of 3-(3,5-dichloro-4-hydroxybenzoyl)-1,1-dioxo-2,3-dihydro-1,3-benzothiazole having characteristic peaks around 7.86, 12.62, 22.54, 24.3, and 32.82 in X-ray powder diffraction (2Θ); an acetone/isopropyl ether solvate of 3-(3,5-dichloro-4-hydroxybenzoyl)-1,1-dioxo-2,3-dihydro-1,3-benzothiazole having characteristic peaks around 7.06, 12.22, 21.66, 23.5, and 24.5 in X-ray powder diffraction (2Θ) and having heat absorption peaks around 88° C. and 212° C. in DSC analysis; a methyltetrahydrofuran solvate of 3-(3,5-dichloro-4-hydroxybenzoyl)-1,1-dioxo-2,3-dihydro-1,3-benzothiazole having characteristic peaks around 9.54, 16.74, 21.02, 22.94, and 26.38 in X-ray powder diffraction (2Θ) and having heat absorption peaks around 97.6° C. and 212° C. in DSC analysis; and a 2-butanone/isopropanol solvate of 3-(3,5-dichloro-4-hydroxybenzoyl)-1,1-dioxo-2,3-dihydro-1,3-benzothiazole having characteristic peaks around 7.86, 12.62, 22.54, 24.3, and 32.82 in X-ray powder diffraction (2Θ).

The X-ray powder diffraction spectrum used in the present invention indicates a spectrum measured using MiniFlex (Rigaku Corporation) under the following conditions:

X-ray source: Cu,
Goniometer: vertical type,
Divergence slit: variable,
Scattering slit: 4.2 deg,
Receiving slit: 0.3 mm,
Scanning mode: continuous,
Scanning speed: 2/min,
Sampling width: 0.01°,
Scan axis: Θ/2Θ, and
Scan range: 3 to 90°

The heat absorption peak in DSC indicates a heat absorption peak measured using DSC220U (Seiko Instruments Inc.) under the following conditions:

Temperature increase rate: 10° C./min,
Atmosphere: nitrogen, and
Measurement temperature range: 30 to 400° C.

The infrared absorption spectrum used in the present invention indicates a spectrum measured using Spectrum One (PerkinElmer Japan Co., Ltd.) under the following conditions:

Measurement method: KBr tablet method, and
Measurement range: 4000 to 400 cm$^{-1}$.

When a type I crystal, a type II crystal, a hydrate, a solvate, and a salt of 3-(3,5-dichloro-4-hydroxybenzoyl)-1,1-dioxo-2,3-dihydro-1,3-benzothiazole are analyzed using the above devices, a substance with data and spectrum patterns similar to those of each crystal form of the present invention is included in the crystal form. In addition, a case where another crystal form is included in an amount undetectable by a common measurement method is also included in a crystal form of the present invention.

The physical property data of e.g. X-ray powder diffraction spectra and DSC analysis can slightly vary depending on crystal growth direction, particle diameter, etc., and measurement conditions. The crystal forms of the present invention should be specified by physical property data described in the specification; however, as described above, the data should not be strictly taken, and a slight change in each physical property data should be included in the scope of rights of the present invention as an acceptable limit.

The "around" described in the physical property data of e.g. X-ray powder diffraction spectra and DSC analysis in the claims and the specification of the present invention means an error range accepted when measuring data, and the error ranges are plus or minus 0.2 in each peak in X-ray powder diffraction (2Θ) and plus or minus 2° C. in peak in DSC analysis. A case where data are matched within the error range is also included in the present invention.

Medicine including a novel crystal form or salt of 3-(3,5-dichloro-4-hydroxybenzoyl)-1,1-dioxo-2,3-dihydro-1,3-benzothiazole as an active ingredient can be directly used, or can be used as a preparation using one, two, or more of preparation additives. The pharmaceutical composition can be used in any dosage form and can be applied as tablets, pills, capsules, powders, fine granules, granules, solutions, suspensions, syrups, injections, external preparations, suppositories, and the like.

When a novel crystal form or salt of 3-(3,5-dichloro-4-hydroxybenzoyl)-1,1-dioxo-2,3-dihydro-1,3-benzothiazole is used as the medicinal preparations described above, the type of preparation additive is not particularly limited, and a base, an excipient, a lubricant, a coating agent, a sugar coating agent, a moistening agent, a binder, a disintegrating agent, a solvent, a solubilizer, a solubilizing agent, a solubilizing aid, a suspending agent, a dispersing agent, an emulsifying agent, a surface active agent, a tonicity agent, a buffering agent, a pH regulator, a soothing agent, a preservative, a preserving agent, a stabilizing agent, an antioxidant, a colorant, a sweetening agent, and the like can be used individually or suitably in combination. Specifically, examples thereof include additives described in Japanese Pharmaceutical Excipients Directory 2007.

The novel crystal forms of 3-(3,5-dichloro-4-hydroxybenzoyl)-1,1-dioxo-2,3-dihydro-1,3-benzothiazole in the present invention have a high level of unchanged compound in urine and a significant uricosuric action, and thus the medicinal compounds or a pharmaceutically acceptable salt thereof, or a hydrate or solvates of the medicinal compounds, are useful as medicine to inhibit reabsorption of uric acid and promote uric acid excretion, are useful as medicine to reduce an uric acid amount and/or uric acid level in blood and tissue, are useful as medicine used for prevention and/or treatment of diseases related to uric acid in blood and/or tissue, are useful as medicine used for prevention and/or treatment of hyperuricemia, and are useful as medicine used for prevention and/or treatment of diseases associated with hyperuricemia and/or diseases accompanied by hyperuricemia.

The dose and frequency of administration of a compound of the present invention or a pharmaceutical composition containing the compound can be properly selected depending on e.g. symptoms, age, sex, dosage forms, and types of concomitant drug, and can be administered once or several times per day in a range of commonly 0.1 to 1000 mg/day/person, preferably 1 to 500 mg/day/person. In addition, the pharmaceutical composition of the present invention can not only be administered alone, but also can be used in combination with another medicine having the same effect and/or another medicine having another effect.

EXAMPLES

The present invention will now be described in detail by way of Examples thereof. It should be noted, however, that the present invention is not limited to the following Examples.

The meanings of abbreviations in Examples are as follows:

$^1$H-NMR: proton nuclear magnetic resonance spectrum, DMSO-d$^6$: deuterated dimethylsulfoxide, Hz: Hertz, J: coupling constant, dd: double doublet, d: doublet, s: singlet, brs: broad singlet, M: molar concentration, and N: normality. It should be noted that NMR indicates 270 MHz nuclear magnetic resonance spectrum, and TMS (tetramethylsilane) was used as an internal standard material.

Example 1 (Method for producing type I crystal): tetrahydrofuran (40 mL) was added to 3-(3,5-dichloro-4-hydroxybenzoyl)-1,1-dioxo-2,3-dihydro-1,3-benzothiazole (10.0 g), which was dissolved by heating, followed by cooling to room temperature. Seed crystals (10 mg) were added to 2-propanol (200 mL), and the obtained mixture was cooled to −25° C. and stirred, and a solution of 3-(3,5-dichloro-4-hydroxybenzoyl)-1,1-dioxo-2,3-dihydro-1,3-benzothiazole in tetrahydrofuran was added dropwise thereto over 15 minutes. The crystals precipitated at 0° C. were collected by filtration and washed with 2-propanol (20 mL), and then dried overnight at 80° C. in vacuo to obtain a type I crystal.

$^1$H-NMRδ (DMSO-d$^6$): 5.36 (2H, s), 7.44 (1H, dd, J=7.6, 7.3 Hz), 7.75 (2H, s), 7.76 (1H, dd, J=8.4, 7.3 Hz), 7.91 (1H, d, J=7.6 Hz), 8.04 (1H, d, J=8.4 Hz), 11.05 (1H, brs).

Example 2 (Method for producing type II crystal): ethyl acetate (45 mL) and 2-propanol (285 mL) were added to 3-(3,5-dichloro-4-hydroxybenzoyl)-1,1-dioxo-2,3-dihydro-1,3-benzothiazole (15.0 g), which was dissolved by heating, followed by cooling to an internal temperature of about 25° C. The precipitated crystals were collected by filtration and washed with 2-propanol (20 mL), and then dried overnight at 100° C. in vacuo to obtain a type II crystal.

$^1$H-NMRδ (DMSO-d$^6$): 5.35 (2H, s), 7.44 (1H, dd, J=7.6, 7.6 Hz), 7.74 (2H, s), 7.76 (1H, dd, J=8.6, 7.6 Hz), 7.90 (1H, d, J=7.6 Hz), 8.03 (1H, d, J=8.6 Hz), 11.05 (1H, brs).

Example 3 (hydrate): 11 mL of a 10% aqueous solution of sodium carbonate was added to a suspension of 3-(3,5-dichloro-4-hydroxybenzoyl)-1,1-dioxo-2,3-dihydro-1,3-benzothiazole (2.50 g) in ethanol (5 mL)/water (25 mL) to dissolve crystals. After cooling to around 15° C., pH 2 was obtained by 1 M hydrochloric acid. The precipitated crystals were collected by filtration and dried overnight at 50° C. in vacuo to obtain a hydrate.

Example 4 (1,2-dimethoxyethane solvate): n-pentane (0.4 mL) was added to a solution of 3-(3,5-dichloro-4-hydroxybenzoyl)-1,1-dioxo-2,3-dihydro-1,3-benzothiazole (41.2 mg) in 1,2-dimethoxyethane (0.4 mL), and the precipitated crystals were collected by filtration and dried in vacuo to obtain a 1,2-dimethoxyethane solvate.

Example 5 (1,4-dioxane solvate): cyclohexane (0.6 mL) was added to a solution of 3-(3,5-dichloro-4-hydroxybenzoyl)-1,1-dioxo-2,3-dihydro-1,3-benzothiazole (40.5 mg) in 1,4-dioxane (0.6 mL), and the precipitated crystals were collected by filtration and dried in vacuo to obtain a 1,4-dioxane solvate.

Example 6 (acetonitrile solvate): 2,2,4-trimethylpentane (3.2 mL) was added to a solution of 3-(3,5-dichloro-4-hydroxybenzoyl)-1,1-dioxo-2,3-dihydro-1,3-benzothiazole (40.7 mg) in acetonitrile (0.8 mL), and the obtained solution was cooled to 5° C. The precipitated crystals were collected by filtration and dried in vacuo to obtain an acetonitrile solvate.

Example 7 (acetone/isopropyl ether solvate): an acetone/isopropyl ether (50:50 v/v) mixed liquid (0.35 mL) was added to 3-(3,5-dichloro-4-hydroxybenzoyl)-1,1-dioxo-2,3-dihydro-1,3-benzothiazole (40.0 mg), which was dissolved by heating at 60° C. for an hour, and the obtained solution was made to pass through a filter. The solvent of the filtrate was distilled under reduced pressure, and drying in vacuo was carried out to obtain an acetone/isopropyl ether solvate.

Example 8 (methyltetrahydrofuran solvate): diethyl ether (0.5 mL) was added to a solution of 3-(3,5-dichloro-4-hydroxybenzoyl)-1,1-dioxo-2,3-dihydro-1,3-benzothiazole (39.3 mg) in methyltetrahydrofuran (0.5 mL), and the precipitated crystals were collected by filtration and dried in vacuo to obtain a methyltetrahydrofuran solvate.

Example 9 (2-butanone solvate): 2-propanol (1.6 mL) was added to a solution of 3-(3,5-dichloro-4-hydroxybenzoyl)-1,1-dioxo-2,3-dihydro-1,3-benzothiazole (41.2 mg) in 2-butanone (0.4 mL), and the obtained solution was left to stand at 5° C. for 48 hours and then concentrated in vacuo to obtain a 2-butanone solvate.

Example 10 (sodium salt): 8 mL of 10% sodium carbonate under ice cooling was added to a solution of 3-(3,5-dichloro-4-hydroxybenzoyl)-1,1-dioxo-2,3-dihydro-1,3-benzothiazole (2.0 g) in an ethanol (10 mL)-water (10 mL) mixed liquid. After adding 10 mL of ethanol, stirring was carried out at room temperature for 3 hours. The suspended crystals were collected by filtration and washed with ethanol, and then dried at 50° C. overnight in vacuo to obtain a sodium salt. Melting point >300° C.

Test Example 1 (flowability and floodability): the compressibility was calculated by measuring bulk density and tap density of the crystals in Examples 1 and 2, and moreover, their dynamic bulk density, angle of repose, angle of spatula, uniformity, cohesion, angle of fall, angle of difference, and degree of dispersion were found, and flowability and floodability were evaluated using the Carr index table. (Table 1).

TABLE 1

Evaluation of flowability and floodability

| Items | Example 1 (after pulverization) | Example 2 (after pulverization) |
| --- | --- | --- |
| Flowability index | 36 | 42 |
| Floodability index | 43 | 49.5 |

Example 2 (type II crystal) is effective to improve industrial operativity and productivity because of excellent flowability and is advantageous because the quality of end products is more uniform. From this, when the crystal of Example 2 (type II crystal) before pulverization was also verified, advantageous results were verified with a flowability index of 65 and a floodability index of 57.5. Furthermore, in Example 2 (type II crystal), less adhesion to a mill when pulverizing the crystal suggested lower electrostatic properties, and operativity was excellent. Therefore, prepotency in industrial production is high in various natures, and Example 2 is useful as a raw material for medication.

Test Example 2 (Absorption Properties at Time of Oral Administration to Rat)

A test substance suspended in a 0.5% solution of methylcellulose was orally administered to a male CD (SD) rat (CHARLES RIVER LABORATORIES JAPAN, INC., 7 weeks old when used) in a dose of 30 and 300 mg/kg, and blood was then collected after 0.25, 0.5, 1, 2, 4, 8, and 24 hours. The level of unchanged compound in blood plasma was measured by HPLC (Table 2, Table 3), and pharmacokinetic parameters were calculated and absorption was evaluated (Table 4).

TABLE 2

Change in unchanged compound level in blood plasma at time of single oral administration to rat

| Dose (mg/kg) | Example | Unchanged compound level in blood plasma (µg/mL) | | | |
| --- | --- | --- | --- | --- | --- |
| | | 0.25 hr | 0.5 hr | 1 hr | 2 hr |
| 30 | 1 | 38.18 ± 23.24 | 58.51 ± 30.81 | 49.75 ± 22.71 | 32.99 ± 10.97 |
| | 2 | 12.45 ± 3.94 | 27.41 ± 4.71 | 37.38 ± 2.85 | 38.54 ± 0.91 |
| 300 | 1 | 174.78 ± 19.03 | 275.88 ± 42.51 | 275.53 ± 30.24 | 298.88 ± 35.19 |
| | 2 | 39.18 ± 4.61 | 79.93 ± 13.24 | 139.63 ± 20.33 | 263.60 ± 42.18 |

Quantification limit level: 0.2 µg/mL, Average value ± standard deviation (n = 4)

TABLE 3

Change in unchanged compound level in blood plasma at time of single oral administration to rat

| Dose (mg/kg) | Example | Unchanged compound level in blood plasma (µg/mL) | | |
| --- | --- | --- | --- | --- |
| | | 4 hr | 8 hr | 24 hr |
| 30 | 1 | 26.58 ± 12.97 | 20.45 ± 5.53 | 1.16 ± 0.45 |
| | 2 | 23.23 ± 3.08 | 19.23 ± 2.51 | 1.35 ± 0.73 |
| 300 | 1 | 285.55 ± 26.38 | 267.85 ± 25.73 | 73.31 ± 27.54 |
| | 2 | 314.28 ± 11.17 | 266.73 ± 38.38 | 47.24 ± 19.93 |

Quantification limit level: 0.2 µg/mL, Average value ± standard deviation (n = 4)

TABLE 4

Pharmacokinetic parameters of unchanged compound at time of single oral administration to rat

| Dose (mg/kg) | Example | $C_{max}$ (µg/mL) | $T_{max}$ (hr) | $AUC_{0-24\,hr}$ (µg · hr/mL) |
| --- | --- | --- | --- | --- |
| 30 | 1 | 59.24 ± 29.54 | 0.63 ± 0.25 | 411.74 ± 123.35 |
| | 2 | 39.03 ± 0.43 | 1.50 ± 0.58 | 371.97 ± 34.08 |
| 300 | 1 | 307.28 ± 26.20 | 4.00 ± 2.83 | 4923.74 ± 547.44 |
| | 2 | 315.53 ± 11.44 | 3.50 ± 1.00 | 4527.88 ± 269.07 |

Average value ± standard deviation (n = 4)

Example of preparation production: an excipient, a binder, a disintegrating agent, a lubricant and the like were added to the compounds described in Examples, and powder was made by wet granulation and tablets were obtained by tableting.

INDUSTRIAL APPLICABILITY

The crystal forms, hydrate, solvates, and salt of 3-(3,5-dichloro-4-hydroxybenzoyl)-1,1-dioxo-2,3-dihydro-1,3- benzothiazole in the present invention are useful as medication because of an excellent uricosuric action.

The crystals of the present invention are extremely easy to handle in industrial production and have physical properties with excellent convenience (for example, excellent flowability and operativity), and in particular, a type II crystal also has prepotency in the industrial production and thus is useful as a raw material for medication.

The invention claimed is:

1. A type II crystal of 3-(3,5-dichloro-4-hydroxybenzoyl)-1,1-dioxo-2,3-dihydro-1,3-benzothiazole, having characteristic peaks at least around 15.1, 18.1, 22.8, 23.7, and 24.0 degrees in a diffraction angle (2θ) by X-ray powder diffraction.

2. The type II crystal according to claim 1, characterized by having a heat absorption peak around 212° C. in DSC analysis.

3. A pharmaceutical composition containing a crystal according to claim 1 and a pharmaceutically acceptable carrier.

4. A method for producing a type II crystal of 3-(3,5-dichloro-4-hydroxybenzoyl)-1,1-dioxo-2,3-dihydro-1,3-benzothiazole, comprising:
crystallization of a compound from an organic solvent to form the type II crystal of 3-(3,5-dichloro-4-hydroxybenzoyl)-1,1-dioxo-2,3-dihydro-1,3-benzothiazole.

5. The method according to claim 4, wherein the organic solvent for crystallization comprises a mixture of a dissolving solvent and a poor solvent.

6. The method according to claim 5, wherein the poor solvent comprises one of 2-propanol, ethanol, n-hexane, cyclohexane, cumene, paraxylene, methylcyclohexane, 2,2,4-trimethylpentane, toluene, n-pentane, n-heptane, and acetonitrile.

7. The method according to claim 5, wherein the dissolving solvent comprises one of tetrahydrofuran, ethyl acetate, and dimethylsulfoxide.

8. The method according to claim 4, further comprising:
dissolving the 3-(3,5-dichloro-4-hydroxybenzoyl)-1,1-dioxo-2,3-dihydro-1,3-benzothiazole compound in the organic solvent by heating.

9. The method according to claim 8, further comprising:
after the step of dissolving the 3-(3,5-dichloro-4-hydroxybenzoyl)-1,1-dioxo-2,3-dihydro-1,3-benzothiazole compound in the organic solvent by heating, cooling the dissolved 3-(3,5-dichloro-4-hydroxybenzoyl)-1,1-dioxo-2,3-dihydro-1,3-benzothiazole compound.

10. The method according to claim 4, wherein the type II crystal of 3-(3,5-dichloro-4-hydroxybenzoyl)-1,1-dioxo-2,3-dihydro-1,3-benzothiazole is characterized by peaks at least around 15.1, 18.1, 22.8, 23.7, and 24.0 degrees in a diffraction angle (2θ) by X-ray powder diffraction.

11. The method according to claim 10, wherein the type II crystal of 3-(3,5-dichloro-4-hydroxybenzoyl)-1,1-dioxo-2,3-dihydro-1,3-benzothiazole is characterized by a heat absorption peak around 212° C. in DSC analysis.

* * * * *

UNITED STATES PATENT AND TRADEMARK OFFICE
CERTIFICATE OF CORRECTION

PATENT NO. : 10,752,601 B2
APPLICATION NO. : 16/482149
DATED : August 25, 2020
INVENTOR(S) : Uda et al.

It is certified that error appears in the above-identified patent and that said Letters Patent is hereby corrected as shown below:

In the Specification

Column 1, Line 58:
"(2Θ)" should be — (2θ) —

Column 2, Line 4:
"(2Θ)" should be — (2θ) —

Column 2, Line 18:
"(2Θ)" should be — (2θ) —

Column 3, Line 62:
"(2Θ)" should be — (2θ) —

Column 3, Line 66:
"(2Θ)" should be — (2θ) —

Column 4, Line 4:
"(2Θ)" should be — (2θ) —

Column 4, Line 7:
"(2Θ)" should be — (2θ) —

Column 4, Line 12:
"(2Θ)" should be — (2θ) —

Column 4, Line 18:
"(2Θ)" should be — (2θ) —

Signed and Sealed this
Twenty-second Day of December, 2020

Andrei Iancu
*Director of the United States Patent and Trademark Office*

Column 4, Line 28:
"2/min," should be — $2°/min,$ —

Column 4, Line 30:
"Θ/2Θ" should be — $θ/2θ$ —

Column 4, Line 67:
"(2Θ)" should be — $(2θ)$ —

In the Claims

Column 9, Claim 1, Line 13:
"(20)" should be — $(2θ)$ —

Column 10, Claim 10, Line 23:
"(20)" should be — $(2θ)$ —